(12) United States Patent
Klinksiek et al.

(10) Patent No.: US 6,331,314 B1
(45) Date of Patent: *Dec. 18, 2001

(54) METHOD AND DEVICE FOR PRODUCING A PARENTERAL MEDICAMENT

(75) Inventors: Bernd Klinksiek; Said Mahiout, both of Bergisch Gladbach; Ricarda-Christine Nothelle, Leverkusen; Hans-Jürgen Hamann, Dormagen; Jürgen Sdebik, Düsseldorf, all of (DE)

(73) Assignee: Bayer Aktiengesellschaft, Leverkusen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,812

(22) PCT Filed: Nov. 4, 1996

(86) PCT No.: PCT/EP96/04795

§ 371 Date: May 12, 1998

§ 102(e) Date: May 12, 1998

(87) PCT Pub. No.: WO97/17946

PCT Pub. Date: May 22, 1997

(30) Foreign Application Priority Data

Nov. 15, 1995 (DE) .................................................. 195 42 499

(51) Int. Cl.$^7$ .................................................... A61K 9/127

(52) U.S. Cl. ..................... 424/450; 264/4.1; 264/4.3; 264/4.6; 428/402.2

(58) Field of Search ................................. 424/400, 1.21, 424/9.321, 9.51, 417, 94.3; 264/4.1, 4.3, 4.6; 428/402.2; 431/829; 935/54

(56) References Cited

U.S. PATENT DOCUMENTS

| 4,529,561 | 7/1985 | Hunt et al. . |
| 4,976,964 | 12/1990 | Schlossmann et al. . |

FOREIGN PATENT DOCUMENTS

| 4207481 | 9/1993 | (DE) . |
| 4328331 | 2/1995 | (DE) . |
| 185756 | 8/1990 | (EP) . |
| 560138 | 9/1993 | (EP) . |
| 83/00089 | 1/1983 | (WO) . |
| 94/08626 | 4/1994 | (WO) . |

OTHER PUBLICATIONS

Martin in Specialized Drug Delivery System Ed. Praveen Tyle Marcel Dekker Inc., 1990.*
Liposome Technology, vol. 1, Chapter 3, "Liposome Preparation Using High–Pressure Homogenizer", Martin Brandl, et al., pp. 49–65.
English Abstract of WO 94/08626, Apr. 28, 1998.

\* cited by examiner

Primary Examiner—Gollamudi S. Kishore
(74) Attorney, Agent, or Firm—Norris McLaughlin & Marcus

(57) ABSTRACT

In the procedure for the production of a formulation of parenterally administrable pharmaceutical preparations, a liposome dispersion is used as a carrier for a pharmaceutical active compound. For the preparation of the liposome dispersion, an aqueous predispersion of one or more amphiphilic substances is fed to a high-pressure homogenizer in which the predispersion is pumped under a pressure from 600 bar to 900 bar through a homogenizer nozzle (2) having a diameter of 0.1 to 0.5 mm. The homogenizer nozzle has an inlet channel (14, 16) and an outlet channel (15, 18) and consists of a hard ceramic plate (11), in which the bore (13) is present, pressed into a steel body (12, 19). The inlet channel (14, 16) and the outlet channel (15, 18) are likewise incorporated into the steel body (12, 19).

11 Claims, 3 Drawing Sheets

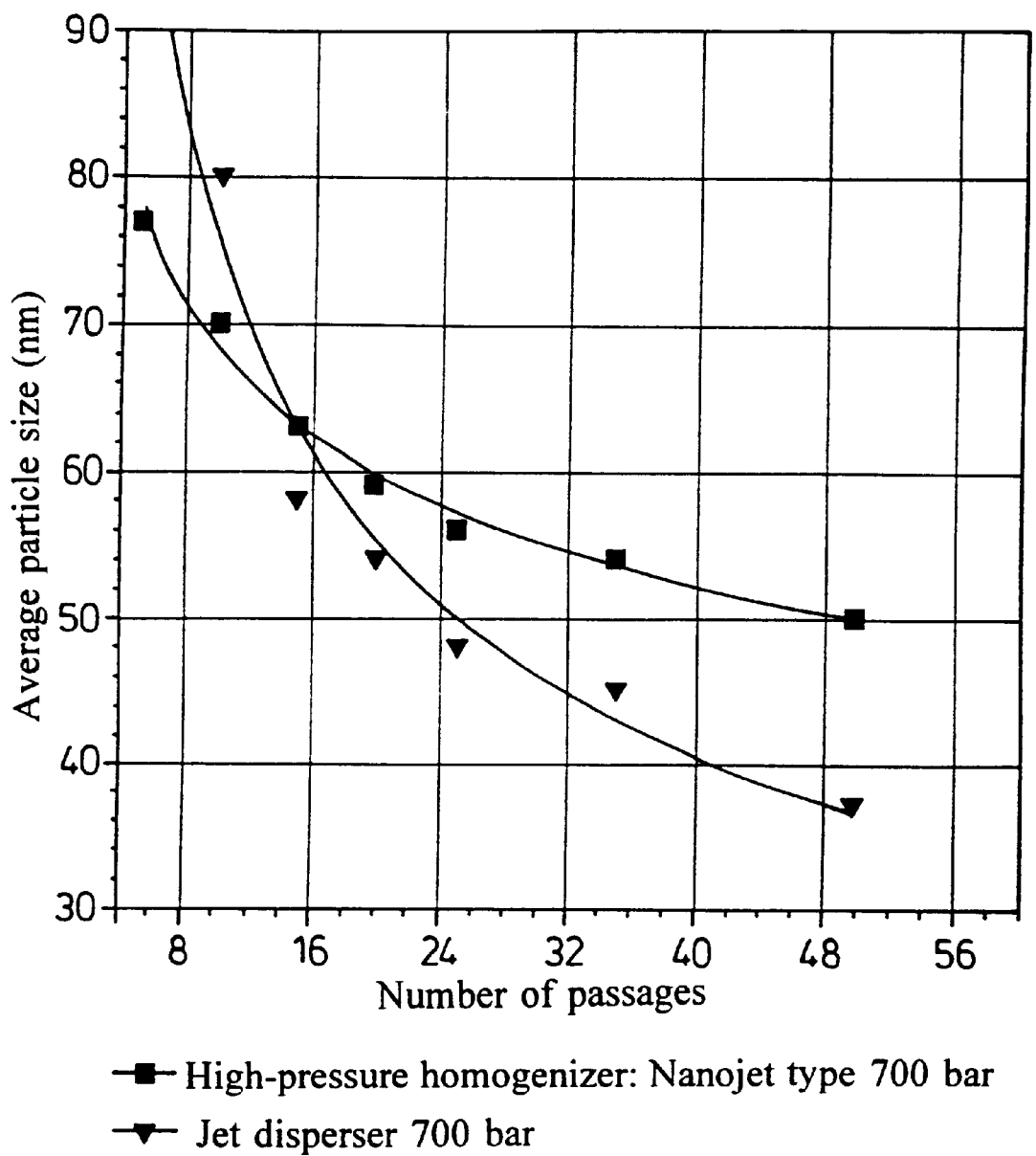

METHOD AND DEVICE FOR PRODUCING A PARENTERAL MEDICAMENT

This application is a 371 of PCT/EP96/04795 filed Nov. 04, 1996.

BACKGROUND OF THE INVENTION

1. Field of the Invention

The invention relates to a procedure for the production of a formulation for parenterally administrable pharmaceutical preparations having a liposome dispersion as a carrier for the pharmaceutical active compound, an aqueous predispersion of amphiphilic substances beings fed to a high-pressure homogenizer for the preparation of the liposome dispersion.

2. Description of Related Art

A large number of procedures have been described for the preparation of liposomes (see, for example, Arndt, "Liposomes", Akademie-Verlag Berlin, 1986). The subject of these studies are often experiments on the laboratory scale. A customary starting process here is the dissolution of phospholipids in organic solvents which are removed again before the homogenization in the course of the further preparation process (DE 35 15 335).

A process of the type described in the foregoing Field of the Invention is described in principle in DE 42 07 481.

In the direct dispersion procedure according to DE 42 07 481, the phospholipid and the crystalline active compound are dispersed directly in water. After swelling of the phospholipids in water coarsely divided liposomes first result, which must then be mechanically comminuted. The active compound deposits or accumulates here on the resulting lipid bilayers of the resulting liposomes. Since many liposome formulations are not heat-sterilizable (particle aggregation, phospholipid hydrolysis), comminution of the liposomes by high-pressure homogenization is necessary until the liposomal dispersion can be sterile-filtered (particle size <200 nm).

Comminution in this case takes place in two steps:

a) First the liposome dispersion is comminuted using a high-speed rotor/stator machine to particle sizes of 500 to 5000 μm.

b) Then a fine comminution takes place to particle sizes of 40 to 100 nm using high-pressure homogenizers known per se.

SUMMARY OF THE INVENTION

The invention is based on the object of developing a procedure for the preparation of liposomes with the finest possible particle size for parenteral administration in reproducible product quality. The liposome dispersion should in this case on the one hand be sterile-filterable without filter residue and on the other hand so fine that the active compound can pass through the finest branchings of the blood vessels on parenteral administration.

This object is achieved according to the invention in that an aqueous predispersion of amphiphilic substances is pumped under a pressure of 500 to 900 bar, preferably 700 bar to 800 bar, through a cylindrical homogenizer nozzle having a diameter of 0.1 mm to 0.5 mm, preferably 0.1 mm to 0.2 mm. Under these conditions, extremely finely particulate dispersions having average particle sizes of 30 nm to 100 nm can be achieved.

Suitable amphiphilic substances are, in particular, phospholipids, cholesterol derivatives and synthetic amphiphiles.

For the preparation of the predispersion, a primary dispersion consisting of the aqueous dispersion containing amphiphilic substances and the pharmaceutical active compound is advantageously pumped through a relatively coarse cylindrical homogenizer nozzle having a diameter of 0.3 mm to 0.7 mm. By this type of prehomogenization, the particle contamination occurring in the rotor/stator machines frequently used until now for predispersion can be avoided.

According to a preferred embodiment, the predispersion is recirculated through the homogenizer nozzle by pumping until the average particle size of the liposome dispersion is in the range between 35 nm and 80 nm with a standard deviation of 3 nm to 7 nm. These particle properties are achieved, in particular, when the predispersion is allowed to flow through the homogenizer nozzle 10 to 30 times in circulation.

Particularly good results are achieved when the dispersion is heated to a temperature in the range from 50° C. to 70° C. in the homogenization circuit by a heat exchanger connected before the homogenizer nozzle.

The storage container is preferably kept at a relatively low temperature level and the dispersion is heated only immediately before the nozzle.

Since energy dissipation and thus warming takes place in the homogenizer nozzle, it is expedient to cool the dispersion again to temperatures in the range from 50° C. to 70° C. immediately after the homogenizer nozzle by means of a heat exchanger connected after it.

For recycling the liposome dispersion, a high-pressure diaphragm-type reciprocating pump is advantageously used which has the advantage that no abrasion and no lubricant can reach the pump chamber, and thus deposit as a contamination source.

The device for carrying out the procedure consists of at least one homogenizer nozzle having an inlet and an outlet channel and is characterized in that the homogenizer nozzle consists of a hard ceramic plate with a bore of 0.1 mm to 0.5 mm, preferably 0.1 mm to 0.2 mm, pressed into a steel body and that the inlet channel to the bore and the outlet channel from the bore are likewise incorporated into the steel body.

In order to achieve high nozzle service lives, hard ceramic plates made of zirconium oxide or silicon carbide are advantageously pressed into the steel body.

According to a further development of the invention, the steel body has several homogenizer nozzles facing one another in pairs, the inlet channels of the homogenizer nozzles being connected in parallel and the outlet channels in the steel body opening into a common collection channel. This embodiment has proved highly suitable, in particular at high throughputs. In this way, an accurate scale-up can be achieved.

The following advantages are achieved by the invention:

Preparation and provision of stable, liposomal formulations, in particular with active compounds which are poorly soluble in water Achievement of a narrow particle size distribution with high reproducibility Gentle treatment, in particular of temperature-sensitive active compounds Problem-free and accurate scale-up due to modular construction of the nozzle homogenizer device Reduction of contamination sources due to minimization of nozzle abrasion and use of a high-pressure diaphragm-type reciprocating pump Good purification possibilities as a result of low gap and dead-space construction Improved service lives of the unit.

BRIEF DESCRIPTION OF THE DRAWINGS

In the following, exemplary embodiments of the invention are illustrated in greater detail with the aid of drawings:

FIG. 5 shows a graphic presentation of the results with exemplary embodiment No. 2.

DETAILED DESCRIPTION OF EXPLARY EMBODIMENT

Figure 1:
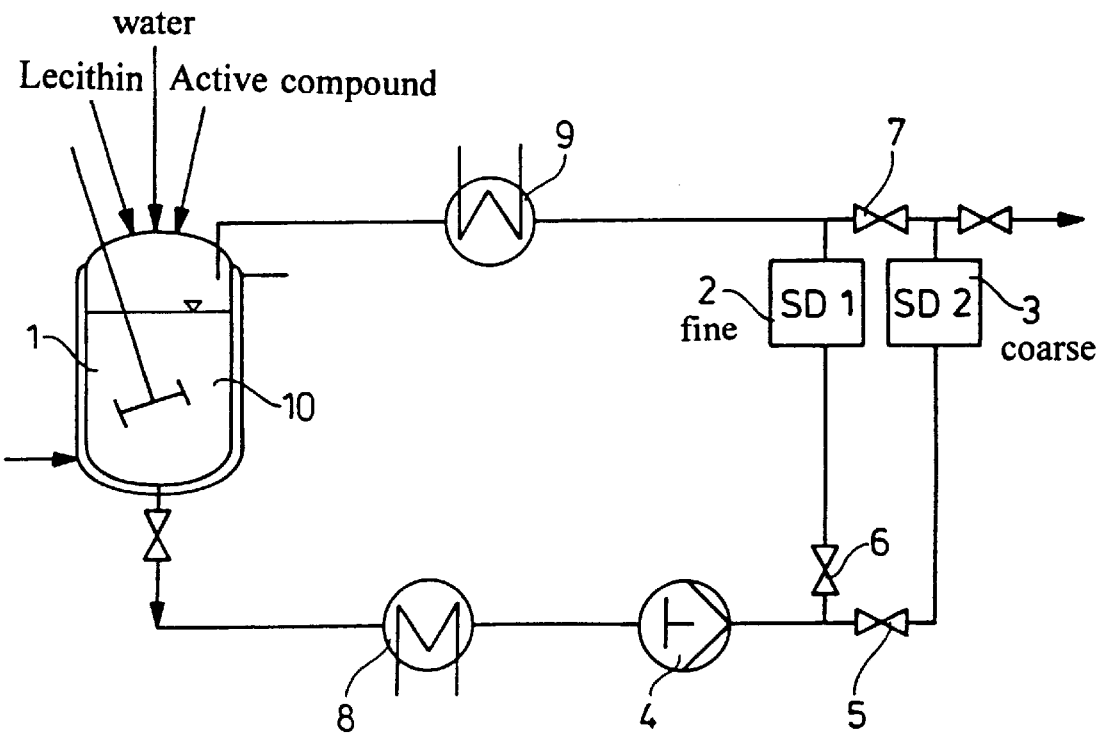
FIG. 1 shows a flow scheme of the unit

According to FIG. 1, a lecithin/water crude dispersion is prepared first by stirring in the heatable and coolable stirring vessel 1 and pumped at temperatures from 50° C. to 70° C. and pressures from 500 to 1000 bar through the homogenizer nozzle 2 having a diameter of 0.2 mm or through the homogenizer nozzle 3 having a diameter of 0.5 mm at pressures from 40 to 200 bar by means of a high-pressure diaphragm-type reciprocating pump 4. Switching over to the desired nozzle 2 or 3 is effected by means of the valves 5, 6 and 7. Since the homogenization proceeds more favourably at 50° C. to 70° C., the mixture is heated beforehand in the heat exchanger 8 and cooled again in the heat exchanger 9 in order to avoid temperature-related product damage, e.g. due to hydrolysis. This cooling is necessary as the dispersion is further heated during passage through the homogenizer nozzle. The temperature in the stirring vessel 1 is kept at a low level ($\leq 50°$ C.) in order to minimize product damage. The active compound is then added and predispersed using the stirrer 10. The primary dispersion prepared in this way is then predispersed by pumping 5 times through the homogenizer nozzle 3 having the larger diameter and then finely dispersed in the circulation through the heat exchangers 8 and 9 and the finer homogenizer nozzle 2. If, for example, after 20 cycles at homogenizer pressures of 500 to 800 bar an average particle size of 35 to 60 nm is achieved, the liposome formulation is pumped off with complete cooling and sterile-filtered.

For the preparation of the predispersion, it is also possible to predisperse all three components water, phospholipid and active compound in the stirring vessel 1 and then to precomminute them in the nozzle 3 before finely homogenizing them through the nozzle 2.

Figure 2:
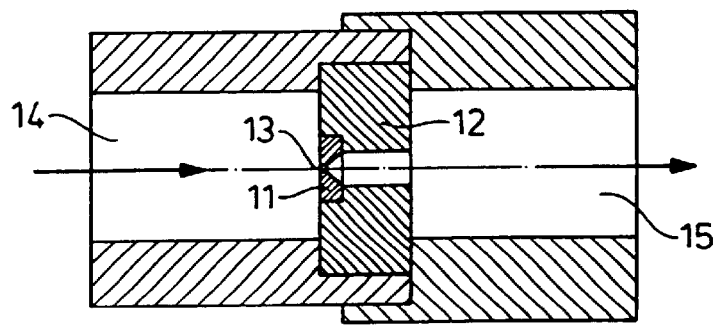
FIG. 2 shows the construction of a homogenizer nozzle

FIG. 2 shows the construction of a homogenizer nozzle in exact detail. It consists of a hard ceramic plate 11, e.g. of zirconium oxide, which is pressed into a steel plate 12, and in the centre has a cylindrical nozzle bore 13 of about 0.2 mm diameter. The nozzle bore 13 widens conically in the flow direction. The inlet 14 for the dispersion is before the nozzle bore 13. The outlet 15 connects to the conical widening. It is important in this embodiment that no opposite wall surfaces are present which can be destroyed by the emerging jet after the nozzle. For this reason, an arrangement is to be preferred in which the nozzles face one another in pairs so that the impulses of the liquid jets mutually balance each other and the residual energy still present can be used for comminution.

Figure 3:
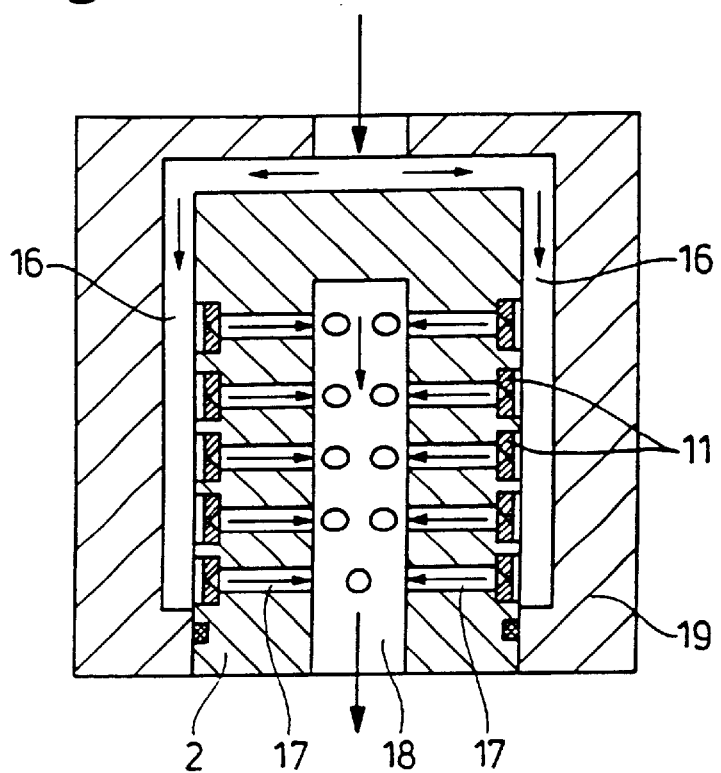
FIG. 3 shows a side view of a nozzle homogenizer consisting of several individual nozzles connected in parallel
Figure 4:
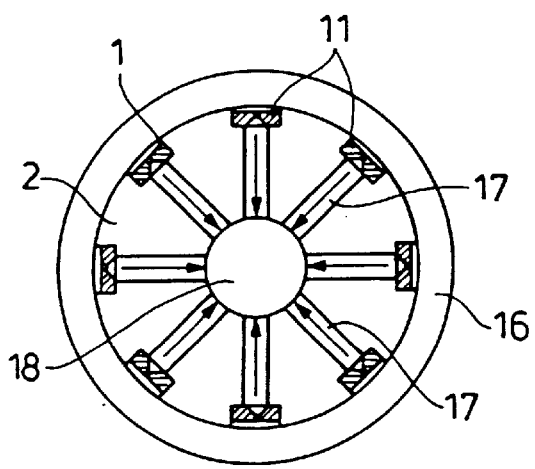
FIG. 4 shows a cross-section through the homogenizer nozzle as shown in FIG. 3

FIGS. 3 and 4 show an embodiment of a nozzle homogenizer for high throughputs with many nozzle bores connected in parallel and facing one another in pairs in a star-shaped, rotationally symmetrical arrangement (see FIG. 4), which are connected to a common annular space supply line 16. The liquid to be dispersed is passed through the annular space supply line 16 and flows after dispersion or homogenization through the outlet channels 17 into a central common collection channel 18. All components 11, 16, 17 and 18 are incorporated into a cylindrical steel block 19.

The ceramic plates 11 with the nozzle bore 13 and the conical widening (see FIG. 2) are manufactured to exact dimensions before pressing into the steel body 12. The bore diameter here is 0.1 to 0.5 mm and the length/diameter ratio 1.5 to 2. As shown in FIGS. 3 and 4, the bore widens to the diameter of the outlet channel 17.

Besides the circular bore in the ceramic disc, nozzles bores with non-circular cross-sections, such as ellipses or slits, are also possible. Also conceivable would be an all ceramic construction. In view of the objective of a reproducible product quality with finest possible particle size and lowest possible wear, however, steel/ceramic composite constructions are most convenient, since significantly higher manufacturing accuracies are achieved, which matters in particular for very high throughputs and in the case of many nozzles connected in parallel.

EXEMPLARY EMBODIMENTS

Example 1

The unit as shown in FIG. 1 is equipped with a stirring vessel 1 having a volume of 6 l, a triple diaphragm-type pump 4, which can achieve at most 900 bar at a throughput of 600 l/h, and with nozzle homogenizers as shown in FIGS. 3 and 4 with two opposite bores of 0.2 mm for the nozzle 2 (SD 1) and with two opposite bores of 0.5 mm diameter for the nozzle 3 (SD 2).

In the stirring vessel 1, 5.59 kg of distilled water are aerated with nitrogen for 30 min. After aeration, 16.2 g of sodium ascorbate are dissolved in water and 580.5 g of purified egg lecithin (phosphatidylcholine >94%) are then added. This mixture is dispersed at 65° C. for 30 min using the high-speed stirrer 10. The dispersion is then homogenized by means of the nozzle 2 in five passages at 800 bar and 65° C. (vessel temperature 50° C.). 145 g of the active compound isopropyl 2-amino-1,4-dihydro-5-cyano-6-methyl-4-(3-phenylquinolin-5-yl)pyridine-3-carboxylate are then added and prehomogenized by means of the nozzle 3 at a pressure of 25 bar and likewise recycled 5 times. The mixture is then homogenized by means of the nozzle 2 by 20 passages at 65° C. and 800 bar preliminary pressure. The average particle size is 48 nm with a standard deviation of 5 nm. The dispersion can be sterile-filtered without problems.

Example 2

According to Example 1, batches are prepared at 700 bar homogenizer pressure using a different number of runs. The results are shown graphically in FIG. 5 and compared with 1 l batches of the same recipe which have been prepared in a laboratory high-pressure homogenizer of the nanojet type. Despite coarser starting particle sizes, using the procedure according to the invention significantly finer particle sizes are achieved with identical homogenizer pressures and an identical number of runs.

Example 3

800 g of water for injection are aerated with nitrogen for 10 min in the stirring vessel. 1 l g of ascorbic acid, 150 g of glucose and 1 g of L-arginine are then dissolved in this amount of water. 1.667 g of nimodipine and 83.35 g of highly pure egg phospholipid (e.g. Lipoid EPC) are dispersed in this medium and it is made up to 1055.5 g using nitrogen-aerated water.

This dispersion is prehomogenized for 30 min at 75° C. under nitrogen protection using a high-speed stirrer, e.g. Ultra-Turrax. It is then homogenized at 75° C. and 800 bar using a device as shown in Example 1 with two opposite sapphire nozzles of 0.2 mm diameter and with a sharp-edged inlet and outlet and a thickness of the sapphire disc of 0.4 mm to 45 nm.

The dispersion is cooled and filled into 250 ml or 50 ml bottles after sterile filtration and freeze-dried.

The lyophilizate can be reconstituted to 250 ml with isotonic glucose solution or to 50 ml with water for injection. The particle size is 50 nm with a standard deviation of 7 nm.

What is claimed is:

1. A process for preparing a parenterally administrable pharmaceutical preparation comprising a liposome dispersion as a carrier for a pharmaceutical active compound, said process comprising preparing the liposome dispersion by a process comprising:

a) feeding an aqueous predispersion comprising one or more amphiphilic substances to a high-pressure homogenizer; and b) pumping the aqueous predispersion under a pressure ranging from 600 bar to 900 bar through a high-pressure homogenizer apparatus;

said high-pressure homogenizer comprising:

i) at least one homogenizer nozzle consisting of a hard ceramic plate pressed into a steel body, said hard ceramic plate comprising a bore having a diameter ranging from 0.1 mm to 0.5 mm;

ii) an inlet channel to the bore incorporated into said steel body; and iii) an outlet channel from the bore incorporated into said steel body.

2. The process according to claim 1, which further comprises preparing the aqueous predispersion by pumping an aqueous dispersion comprising the one or more amphiphilic substances and a primary dispersion comprising the pharmaceutical active compound through a second homogenizer nozzle having a diameter ranging from 0.3 mm to 0.7 mm.

3. The process according to claim 1, wherein the homogenizer nozzle has a diameter ranging from 0.1 mm to 0.2 mm, and the process further comprises recirculating the aqueous predispersion through the homogenizer nozzle having a diameter ranging from 0.1 mm to 0.2 mm by pumping until the liposome dispersion attains an average particle size ranging between 35 nm and 80 nm with a standard deviation of 4 nm to 8 nm.

4. The process according to claim 3, which further comprises recirculating the aqueous predispersion through the homogenizer nozzle having a diameter ranging from 0.1 nm to 0.2 nm from 10 to 30 times.

5. The process according to claim 3, which further comprises heating the aqueous predispersion to a temperature ranging from 50° C. to 70° C. by a heat exchanger in line before the homogenizer nozzle having a diameter ranging from 0.1 mm to 0.2 mm.

6. The process according to claim 3, which further comprises combining components of the aqueous predispersion in a stirring vessel, which stirring vessel is maintained at a temperature of $\leq 50°$ C.

7. The process according to claim 3, which further comprises cooling the aqueous predispersion to a temperature ranting from 50° C. to 70° C. by a heat exchanger in line after the homogenizer nozzle having a diameter ranging from 0.1 mm to 0.2 mm.

8. The process according to claim 2, wherein said pumping is effected by a diaphragm pump.

9. The process according to claim 2, which comprises preparing the liposome dispersion by feeding an aqueous predispersion comprising one or more amphiphilic substances to a high-pressure homogenizer, and pumping the aqueous predispersion under a pressure ranging from 700 bar to 800 bar through a homogenizer nozzle having a diameter ranging from 0.1 mm to 0.2 mm.

10. The process according to claim 2, wherein the hard ceramic plate consists of zirconium oxide or silicon carbide.

11. The process according to claim 2, wherein the steel body has several homogenizer nozzles facing each other in pairs, with the inlet channels thereof connected in parallel, and the outlet channels thereof opening into a common collection channel.

* * * * *